United States Patent
Barasch et al.

(10) Patent No.: US 7,022,666 B1
(45) Date of Patent: Apr. 4, 2006

(54) METHOD OF INDUCING FORMATION OF KIDNEY EPITHELIA FROM MESENCHYMAL PRECURSORS

(75) Inventors: Jonathan M. Barasch, New York, NY (US); Juan A. Oliver, New York, NY (US); Jun Yang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/980,853

(22) PCT Filed: May 4, 2000

(86) PCT No.: PCT/US00/12536

§ 371 (c)(1),
(2), (4) Date: Mar. 12, 2002

(87) PCT Pub. No.: WO00/66147

PCT Pub. Date: Nov. 9, 2000

Related U.S. Application Data

(63) Continuation-in-part of application No. 09/305,029, filed on May 4, 1999, now Pat. No. 6,423,681.

(51) Int. Cl.
*A61K 38/18* (2006.01)

(52) U.S. Cl. .......................................... 514/2; 514/21

(58) Field of Classification Search ................ 514/2, 514/21
See application file for complete search history.

(56) References Cited

U.S. PATENT DOCUMENTS 5,202,116 A * 4/1993 Brown et al. ............... 424/85.1

FOREIGN PATENT DOCUMENTS

WO          0041713        7/2000

OTHER PUBLICATIONS

Barasch, J., L. Pressler, J. Connor, and A. Malik. 1996. A ureteric bud cell line induces nephrogenesis in two steps by two distinct signals. *Am. J. Physiol.* 271: F50--F61.
Barasch, J., J. Qioa, G. McWilliams, D. Chen, J.A. Oliver, and D. Herzlinger. 1997. Ureteric bud cells secrete multiple factors, including bFGF, which resue renal progenitors from apoptosis. *Am. J. Physiol.* 273: F757-F767.
Barasch, J., J. Yang, J. Qiao, P. Tempst, H. Erdjument-Bromage, W. Leung, J.A. Oliver. May, 1999. Tissue inhibitor of metallaproteinase-2 stimulates mesenchymal growth and regulates epithelial branching during morphogenesis of the rat metanephros. *J. Clin. Invest.* 103: 1299-1307.

Bard, J.B.L. and A.S.A. Ross. LIF, the ES-cell inhibition factor, reversibly blocks nephrogenesis in cultured mouse kidney rudiments. Development 113: 193-198, 1991.
Boccaccio, C., M. Ando, L.Tamagnone, A. Bardelli, P. Michieli, C. Battistini, and P.M. Comoglio. 1998. Induction of epithelial tubules by growth factor HGF depends on the STAT pathway. *Nature* 391: 285-288.
Bonni, A., Y. Sun, M. Nadal-Vicens, A. Bhatt, D. A. Frank, I. Rozovsky, N. Stahl, G.D. Yancopoulos, and M.E. Greenberg. 1997. Regulation of gliogenesis in the central nervous system by the JAK-STAT signaling pathway. *Science* 278: 477-483.
Grobstein, C. 1955. Inductive interaction in the development of the mouse metanephros. *J. Exp. Zool.* 130: 319-339.
Gruenwald, P. 1943. Stimulation of nephrogenic tissue by normal and abnormal inductors. *Anat. Rec.* 86: 321-335.
Hartner, A. et al. Cytokine-induced expression of leukemia inhibitory factor in renal mesangial cells. Kidney International 45: 1562-1571, 1994.
Hartner, A. et al. Renal mesangial cells have the capacity to synthesize and react to leukemia inhibitory factor. Ann. N.Y. Acad. Sci. 762 (Interleukin-6-Type Cytokines) : 424-425, 1995 (Abstract).
Herzlinger, D., J. Qiao, D. Cohen, N. Ramakrishna, and A.M.C. Brown, 1994. Induction of Kidney epithelial morphogenesis by cells expressing Wnt-1. *Develop. Biol.* 166: 815-818.
Karavanova, I.D., L.F. Dove, J.H. Resau, and A.O. Perantoni. 1996. Conditioned media from a rat ureteric bud cell line in combination with bFGF induces complete differentiation of isolated metanephric mesenchyme. *Development* 122: 4159-4167.
Kispert, A., S. Vainio, A.P. McMahon. 1998. Wnt-4 is a mesenchymal signal for epithelial transformation of metanephric mesenchyme in the developing kidney. *Development* 125; 4225-4234.
Mayer, M., Bhakoo, K., and M. Noble. 1994. Ciliary Neurotrophic factor and leukemia inhibitory factor promote the generation, maturation and survival of oligodendrocytes in vitro. *Development* 120: 143-153.
Morel, D.S. et al. Renal synthesis of leukemia inhibitory factor. Cytokine 12 (3) : 265-271, 2000 (Abstract).
Murphy, M., K. Reid, D.J. Hilton, and P.F. Bartlett. 1991. Generation of sensory neurons is stimulated by leukemia inhibitory factor. *Proc. Natl. Acd. Sci.* USA 88: 3498-3501.

(Continued)

Primary Examiner—Jean C. Witz
(74) *Attorney, Agent, or Firm*—John P. White, Esq.; Cooper & Dunham LLP

(57) ABSTRACT

This invention provides methods of using a gp130 receptor ligand, e.g. leukemia inhibitory factor, to induce the formation of kidney epithelia, to treat subjects suffering from kidney failure, and to preserve kidneys for transplantation.

5 Claims, 9 Drawing Sheets

OTHER PUBLICATIONS

Murphy, M., K. Reid, M.A. Brown, P.F. Bartlett. 1993 Involvement of leukemia inhibitory factor and nerve growth factor in the development of dorsal root ganglion neurons. *Development* 117: 1173-1182.

Murphy, M., K. Reid, M. Ford, J. B. Furness, and P. F. Bartlett. 1994. FGF2 regulates proliferation of neural crest cells, with subsequent neuronal differentiation regulated by LIF or related factors, *Development* 120: 3519-3528.

Perantoni, A.O., L.F. Dove and I. Karavanova. 1995. Basic fibroblast growth factor can mediate the early inductive events in renal development. *Proc. Natl. Acad. Sci.* USA. 92: 4696-4700.

Sariola, H., P. Ekblom, S. Henke-Fahle. 1989. Embryonic neurons as in vitro inducers of differentiation of nephrogenic mesenchyme. *Devel. Biol.* 132: 271-281.

Stark, K., S. Vainio, G. Vassileva, A. P. McMahon. 1994. Epithelial transformation of metanephric mesenchyme in the developing kidney regulated by *Wnt-4. Nature* 372: 679-683.

Taupin, J.L. et al. HILDA-LIF urinary excretion during acute kidney rejection. Transplantation 53 (3) : 655-658, 1992 (Abstract).

Wallner, E. I. et al. Growth factors in metanephric development. Renal Failure 20(2) : 331-341, 1998 (Abstract).

* cited by examiner (+) FGF-2/TGFα     (+) Conditioned Media (+) FGF-2/TGFα

(+)LIF (+)FGF-2/TGFα

E – Cadherin

E – Cadherin          E – Cadherin/Collagen IV (+) LIF (+) FGF-2/TGFα

```
                        SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      primer/probe

<400> SEQUENCE: 1
caatgccctc tttatttcc                                                  19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 2
acttgcttgt atgtcccc                                                   18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 3
tgaagtggaa tgacaaaggg                                                 20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      primer/probe

<400> SEQUENCE: 4
aagatggata agagggcgg                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      primer/probe
```

```
<400> SEQUENCE: 5
acacagtcca agtcagtttc                                                    20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 6
atccttccca ccttcttc                                                      18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      primer/probe

<400> SEQUENCE: 7
ggaagtgatt cgaaatgatg tg                                                 22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      primer/probe

<400> SEQUENCE: 8
tcagaaccac tcccctcata g                                                  21
```

METHOD OF INDUCING FORMATION OF KIDNEY EPITHELIA FROM MESENCHYMAL PRECURSORS

This application is a §371 national stage of PCT International Application No. PCT/US00/12536, filed May 4, 2000, which is a continuation-in-part and claims benefit of U.S. Ser. No. 09/305,029, filed May 4, 1999, now U.S. Pat. No. 6,423,681 issued Jul. 23, 2002, the contents of which are hereby incorporated by reference.

The invention disclosed herein was made with Government support under grant numbers DK 555388 and DK 46934 from the National Institutes of Health, U.S. Department of Health and Human Services. Accordingly, the U.S. Government has certain rights in this invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The kidney develops from two components, the metanephric mesenchyme and the ureteric bud. The ureteric bud invades the mesenchyme, triggering both mesenchymal proliferation and the conversion of the mesenchyme into epithelia. This process has been termed induction of the mesenchyme (Grobstein, 1955; Saxen, 1987; Ekblom, 1989). The bud is known to produce factors which stimulate growth of the metanephric mesenchyme (Perantoni et al., 1995; Barasch et al., 1997), but the ureteric factors which convert mesenchyme into epithelia have been unknown. To date, induction of isolated metanephric mesenchyme in vitro has been obtained with living cells, including a number of embryonic tissues (Grobstein, 1955; Sariola et al., 1989; Herzlinger et al., 1994; Kispert et al., 1998), but not with purified molecules.

To identify ureteric factors that trigger mesenchymal induction, we developed ureteric bud cell lines (UB cells; Barasch et al., 1996). These cells express a number of proteins in common with the embryonic ureteric bud at the time it invades the mesenchyme, including epithelial specific proteins (E-cadherin, ZO-1, cytokeratin, collagen IV, and laminin), receptor tyrosine kinases (c-ret and c-met), lectin (dolichos bifloris) binding sites (Barasch et al., 1996; Sakuri et al., 1997), as well as several monoclonal binding sites which cross react with the ureteric bud. In addition, UB cells secrete a number of metanephric mesenchymal growth factors (FGF-2, FGF-9, TIMP-1 and TIMP-2) that are also synthesized by the embryonic ureteric bud (Barasch et al, 1997; Barasch et al., 1999). We previously found that UB cells secrete factors (Barasch et al., 1997) that stimulate mesenchymal growth but cannot trigger metanephric mesenchymal conversion to epithelia.

The present application discloses the following. UB cells secrete several activities that in the presence of mesenchymal growth factors (Karavanova et al., 1996) trigger mesenchymal to epithelial conversion and tubulogenesis.

Purification and sequencing of one activity identified leukemia inhibitory factor (LIF). Metanephric mesenchymes treated with recombinant LIF (rLIF) were converted into epithelia and developed tubules as well as early nephrons. Other cytokines that signal through the gp130 receptor, like LIF, were also shown to induce epithelia. In vivo, LIF is expressed by the ureteric bud during invasion of the metanephric mesenchyme, while LIF receptors are expressed by the mesenchyme. Thus, as disclosed in the present application, LIF is a candidate mediator of epithelialization and morphogenesis in the embryonic kidney.

SUMMARY OF THE INVENTION

This invention is directed to a method of inducing the formation of kidney epithelia which comprises contacting mesenchymal precursors, in the presence of a growth factor, with an amount of a gp130 receptor ligand effective to induce the formation of kidney epithelia. This invention is the first disclosure of a method of inducing the formation of kidney epithelia with purified molecules.

This invention also provides a method of inducing the formation of kidney epithelia which consists essentially of contacting mesenchymal precursors, in the presence of a growth factor, with an amount of a purified gp130 receptor ligand effective to induce the formation of kidney epithelia.

This invention provides a method of inducing the differentiation of fetal tissue, fetal cells, or fetal or postnatal precursor or stem cells into kidney nephrons in a subject with diminished kidney function, which comprises administering to the subject, in the presence of a growth factor, an amount of a gp130 receptor ligand effective to induce differentiation of such fetal tissue, fetal cells, or fetal or postnatal precursor or stem cells into kidney nephrons.

This invention provides a method of treating a subject suffering from kidney failure which comprises administering to the subject, in the presence of a growth factor, an amount of a gp130 receptor ligand effective to treat the subject's kidney failure.

This invention provides a method of preserving a kidney for transplantation which comprises contacting the kidney, in the presence of a growth factor, with an amount of a gp130 receptor ligand effective to preserve the kidney.

DETAILED DESCRIPTION OF THE INVENTION

Figure 1:
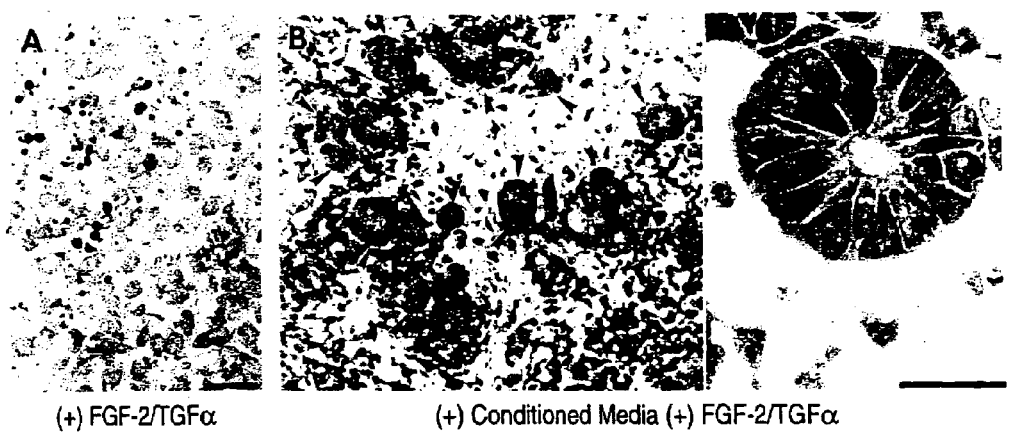
FIG. 1. Conversion of metanephric mesenchyme to epithelia. Isolated metanephric mesenchymes were cultured in serum free media (Karavanova et al., 1996), supplemented with FGF-2 (50 ng/ml) plus TGFα (10 ng/ml) or additionally with media conditioned by UB cells (100 μg/ml). The mesenchymes were analyzed after 7 days in culture.
A. Metanephric mesenchymal cells are rescued from apoptosis by incubation with FGF-2/TGFα, but do not show epithelial organization (Left: Bar=20 μm)
B. Metanephric mesenchyme incubated with FGF-2/TGFα plus UB cell conditioned media. Mesenchymal cells are organized in epithelialized aggregates (arrowheads), including C-shaped bodies (arrows). High power shows polarized epithelia (Far right) Bars=20 μm.

The following definitions are presented as an aid in understanding this invention.

As used herein a gp130 receptor ligand means a protein ligand (polypeptide) that transduces a signal through the gp130 receptor. These protein ligands include leukemia inhibitory factor (Moreau et al., 1988), cardiotrophin (Sheng et al., 1996), oncostatin M (Malik et al., 1989), ciliary neuronotrophic factor (Mayer et al., 1994), and interleukin-6 (Faulds et al., 1998; Wong et al., 1988). The term gp130 receptor ligand is used to include both naturally occurring gp130 receptor ligands and gp130 receptor ligands which are synthesized using recombinant DNA technology. Synthesized polypeptides may differ from their naturally occurring counterparts, for example, in terms of their acetylation, glycosylation, and/or disulfide bonds.

A leukemia inhibitory factor is a member of the cytokine family that includes cardiotrophin, oncostatin M, ciliary neuronotrophic factor, and interleukin-6. All of these cytokines use gp130 receptors for signaling. The term leukemia inhibitory factor is used to include both a naturally occurring leukemia inhibitory factor and a leukemia inhibitory factor which is synthesized using recombinant DNA technology. Synthesized polypeptides may differ from their naturally occurring counterparts, for example, in terms of their acetylation, glycosylation, and/or disulfide bonds.

A growth factor means a protein that binds to cell surface receptors and is required for cell survival or proliferation. Growth factors include transforming growth factor-α (TGFα), fibroblast growth factors-2 and -9 (FGF-2, FGF-9) (Barasch et al., 1997; Karavanova et al., 1996; Kurokawa et al., 1987; Miyamoto et al., 1993; Perantoni et al., 1995), and tissue inhibitors of metalloproteinases-1 and -2 (TIMP-1, TIMP-2) (Barasch et al., 1999; Stetler-Stevenson et al., 1990). The term growth factor is used to include both naturally occurring growth factors and growth factors which are synthesized using recombinant DNA technology. Synthesized polypeptides may differ from their naturally occurring counterparts, for example, in terms of their acetylation, glycosylation, and/or disulfide bonds.

The binding of gp130 ligands requires a receptor(s) in addition to gp130, which interacts with gp130. These co-receptors include but are not limited to leukemia inhibitory factor receptor, the oncostatin receptor, ciliary neuronotrophic factor receptor, and the interleukin-6 receptor. As disclosed in the present application, gp130 receptor ligands induce epithelial cells to form and organize into nephrons from epithelial progenitor cells in the metanephric kidney, and the growth factors TGFα, FGF-2, FGF-9, TIMP-1, and TIMP-2 bind to the cell surface of metanephric mesenchymal cells and maintain their viability.

Having due regard to the preceding definitions, the present invention concerns a method of inducing the formation of kidney epithelia which comprises contacting mesenchymal precursors, in the presence of a growth factor, with an amount of a gp130 receptor ligand effective to induce the formation of kidney epithelia. This invention is the first disclosure of a method of inducing the formation of kidney epithelia with purified molecules.

This invention also provides a method of inducing the formation of kidney epithelia which consists essentially of contacting mesenchymal precursors, in the presence of a growth factor, with an amount of a purified gp130 receptor ligand effective to induce the formation of kidney epithelia.

In one embodiment, the gp130 receptor ligand is a leukemia inhibitory factor.

This invention provides a method of inducing the differentiation of fetal tissue, fetal cells, or fetal or postnatal precursor or stem cells into kidney nephrons in a subject with diminished kidney function, which comprises administering to the subject, in the presence of a growth factor, an amount of a gp130 receptor ligand effective to induce differentiation of such fetal tissue, fetal cells, or fetal or postnatal precursor or stem cells into kidney nephrons. In one embodiment, the fetal tissue, fetal cells, or fetal or postnatal precursor or stem cells are treated with a gp130 receptor ligand ex vivo, in the presence of a growth factor, and the so treated fetal tissue, fetal cells, or fetal or postnatal precursor or stem cells are then transplanted into the subject with diminished kidney function.

In one embodiment, the gp130 receptor ligand is a leukemia inhibitory factor.

This invention provides a method of treating a subject suffering from kidney failure which comprises administering to the subject, in the presence of a growth factor, an amount of a gp130 receptor ligand effective to treat the subject's kidney failure.

This invention provides a method of using a gp130 receptor ligand to stimulate endogenous kidney progenitors to differentiate into kidney nephrons for the purpose of restoring kidney function in a subject with diminished kidney function which comprises administering to the subject an amount of a gp130 receptor ligand effective to restore the subject's kidney function.

In one embodiment, the gp130 receptor ligand is a leukemia inhibitory factor.

This invention provides a method of preserving a kidney for transplantation which comprises contacting the kidney, in the presence of a growth factor, with an amount of a gp130 receptor ligand effective to preserve the kidney. In one embodiment, the method is used to preserve a kidney during shipment. In a preferred embodiment, the method ameliorates or prevents acute tubular necrosis.

In one embodiment, the gp130 receptor ligand is a leukemia inhibitory factor.

In one embodiment involving ex vivo use of a gp130 receptor ligand, the effective amount of the gp130 receptor ligand is an amount from about 5 ng/ml to about 200 ng/ml. In another embodiment involving administration of a gp130 receptor ligand to a subject, the effective amount of the gp130 receptor ligand is an amount from about 1 µg/kg to about 50 µg/kg of body weight.

In one embodiment, the gp130 receptor ligand is a cardiotrophin, an oncostatin M, a ciliary neuronotrophic factor, or an interleukin-6.

In one embodiment, the growth factor is one or more of a TGFα, a FGF-2, a FGF-9, a TIMP-1, or a TIMP-2. In one embodiment involving ex vivo use of TGFα, FGF-2, or FGF-9, the effective amount of TGFα, FGF-2, or FGF-9 is an amount from about 1 ng/ml to about 100 ng/ml. In another embodiment involving administration of TGFα, FGF-2, or FGF-9 to a subject, the effective amount of TGFα, FGF-2, or FGF-9 is an amount from about 0.1 mg/kg to about 25 µg/kg of body weight. In one embodiment involving ex vivo use of TIMP-1 or TIMP-2, the effective amount of TIMP-1 or TIMP-2 is an amount from about 200 ng/ml to about 2 µg/ml. In another embodiment involving administration of TIMP-1 or TIMP-2 to a subject, the effective amount of TIMP-1 or TIMP-2 is an amount from about 25 µg/kg to about 500 g/kg of body weight.

In one embodiment, the gp130 receptor ligand is a polypeptide comprising a sequence identical to a naturally occurring human gp130 receptor ligand.

In one embodiment, the leukemia inhibitory factor is a polypeptide comprising a sequence identical to a naturally occurring human leukemia inhibitory factor.

In one embodiment, the growth factor is a polypeptide comprising a sequence identical to a naturally occurring human growth factor.

Human sequences have been determined for leukemia inhibitory factor (Moreau et al., 1988), oncostatin M (Malik et al., 1989), interleukin-6 (Faulds et al., 1998; Wong et al., 1988), leukemia inhibitory factor receptor (Gearing et al., 1991), gp130 receptor (Hibi et al., 1990), FGF-2 (Kurokawa et al., 1987), FGF-9 (Miyamoto et al., 1993), and TIMP-2 (Stetler-Stevenson et al., 1990).

One embodiment of the invention uses polypeptides synthesized using recombinant DNA technology. Such synthesized polypeptides may differ from their naturally occurring counterparts, for example, in terms of their acetylation, glycosylation, and/or disulfide bonds.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Assay of Mesenchymal to Epithelial Conversion

Media conditioned by UB cells, fractions of this media, as well as commercial cytokines (R&D Systems; Minneapolis, Minn.) were assayed using metanephric mesenchymes from the $E_{13}$ rat metanephros as described in Barasch et al., 1996. In brief, five metanephric mesenchymes were isolated from their ureteric buds and cultured on Costar filters in serum free media, supplemented with FGF-2 (50 ng/ml) and TGFα (10 ng/ml) (Karavanova et al., 1996) plus the test fraction.

Conversion of the metanephric mesenchyme into epithelia was assayed by 1) immunocytochemistry for epithelial markers cytokeratin (pan-cytokeratin, Sigma, St. Louis, Mo.), E-cadherin (Transduction Labs, Lexington, Ky.) and collagen IV (Biodesign, Kennebunk, Me.) in whole mounts of mesenchymes fixed in methanol, 2) immunoblots against cytokeratin and E-cadherin (with the same antibodies) using 20 µg of protein from metanephric mesenchymes, and 3) electron microscopy of Epon embedded mesenchymes. The possibility of contamination by fragments of the ureteric bud was ruled out by staining with Dolichos bifloris lectin (Vector Labs, Burlingame, Calif.) using 2% paraformaldehyde fixed tissues permeabilized with 0.07% saponin (Gilbert et al., 1996).

To determine if epithelia were induced by brief exposure to LIF, metanephric mesenchymes were treated with recombinant LIF (rLIF; R&D Systems, Minneapolis, Minn.) for different times and then washed and recultured with FGF-2 and TGFα plus anti-LIF neutralizing antibodies (20 µg/ml; R&D Systems). Alternatively, a suspension of single cells was prepared from mesenchymes treated with rLIF using enzymatic dissociation (Herzlinger et al., 1992) and the cells were then plated on collagen coated filters in serum free media supplemented with FGF-2 and TGFα.

To assay whether LIF stimulates growth of the metanephric mesenchyme, H-thymidine (10 µCi/ml; New England Nuclear, Boston, Mass.) was added to isolated mesenchymes treated with rLIF (1–500 ng/ml) as described in Barasch et al., 1997.

Isolation and Identification of Leukemia Inhibitory Factor (LIF)

50 liters of serum free conditioned media were generated from monolayers of UB cells, concentrated, desalted and applied to heparin-Sepharose (Pharmacia, Piscataway, N.J.) in 10 mM Na PO, pH 7.0. Bound proteins were eluted by a linear gradient of NaCl in the same buffer, as described in Barasch et al., 1997. Activity eluted at ~0.1 M NaCl, and after desalting, these factors were rerun on a second heparin-Sepharose column with a swallower NaCl gradient in the same buffer. The most active fraction was injected to a Mono Q column (Pharmacia) in 20 mM Tris, 1 mM ethanolamine, pH 9.2 and eluted in a NaCl gradient in the same buffer. The active fraction was separated by chromatofocusing with a Mono P column (Pharmacia; buffer A: 25 mM triethanolamine, pH 8.35; buffer B: 9 ml polybuffer 96, 0.21 ml pharmalyte, pH 6.0); activity eluted at a pH of 7.65. This fraction was resolved by gel filtration using a Superdex-75 SMART column (Pharmacia) in 150 mM NaCl, 50 mM $NaPO_4$, 10% sucrose, pH 7.0. Activity was recovered at 46 kDa. The final fraction was concentrated by evaporation and loaded on a 10% polyacrylamide-SDS gel and the protein finally transferred to nitrocellulose.

Peptides were generated from the nitrocellulose bound protein by in-situ tryptic digestion (Lui et al., 1996) and fractionated by reversed-phase HPLC using a 0.8-mm Vydac C-18 column (LC-Packings, San Francisco Calif.; Elicone et al., 1994; Tempst et al., 1994). Selected peak fractions were then analyzed by a combination of delayed extraction matrix-assisted laser-desorption/ionization reflectron time-of flight mass spectrometry (MALDI re-TOF MS; REFLEX III, Bruker-Franzen; Bremen, Germany) and automated Edman sequencing 477 A (Applied Biosystems, Foster City, Calif.; Erdjument-Bromage et al., 1998). Partial peptide sequences were compared to entries in both the non-redundant ('nr') and 'dbEST' databases from the National Center for Biotechnology Information (NCBI) using the Blast program (Altschul et al., 1990). After matches with LIF had been found, mass analysis of several more peptides was done and the results compared to the published sequences by mass-fitting using PeptideSearch software (provided by Dr. Matthias Mann; Odense University, Denmark).

RT-PCR

To localize LIF, LIF receptor, and gp-130 in the metanephric mesenchyme and in the ureteric bud, 50 rat mesenchymes dissected at day 12 of embryonic life ($E_{12}$), just before the invasion of the metanephric mesenchyme by the ureteric bud, and 400 ureteric buds from $E_{12.5}$, just after the bud branches from the Wolffian Duct, were subjected to RT-PCR.

The following primers were used for LIF:
forward: 5'CAATGCCCTCTTTATTTCC (SEQ ID NO: 1),
reverse: 5'ACTTGCTTGTATGTCCCC (SEQ ID NO: 2).

The following primers were used for LIF receptor:
forward: 5'TGAAGTGGAATGACAAAGGG (SEQ ID NO: 3)
reverse: 5'AAGATGGATAAGAGGGCGG (SEQ ID NO: 4).

The following primers were used for gp130:
forward: 5'ACACAGTCCAAGTCAGTTTC (SEQ ID NO: 5)
reverse: 5'ATCCTTCCCACCTTCTTC (SEQ ID NO: 6).

Each reaction used 0.2 µg of poly A RNA and 30 cycles. Sequencing authenticated the product of each reaction.

For E-cadherin detection, RT-PCR from poly A RNA from cultured mesenchymes used the following primers:
forward: 5'GGAAGTGATTCGAAATGATGTG (SEQ ID NO: 7),
reverse: 5' TCAGAACCACTCCCCTCATAG (SEQ ID NO: 8)

Results

Figure 2:
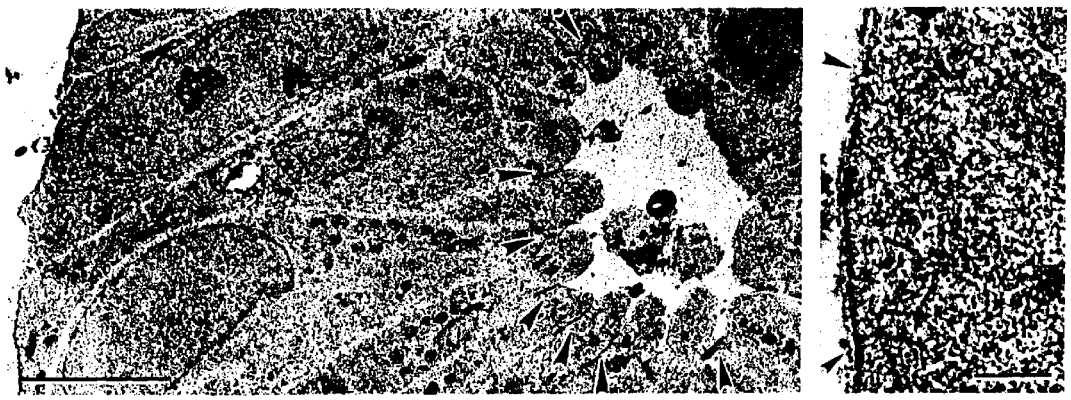
FIG. 2. UB cell conditioned media induced polarized epithelia in metanephric mesenchyme. Electron micrographs show a tubule with a central lumen, apically located intercellular junctional complexes (left, arrowheads; Bar=5 μm) and basement matrix (right, arrowheads; Bar=0.625 μm)
Figure 3:
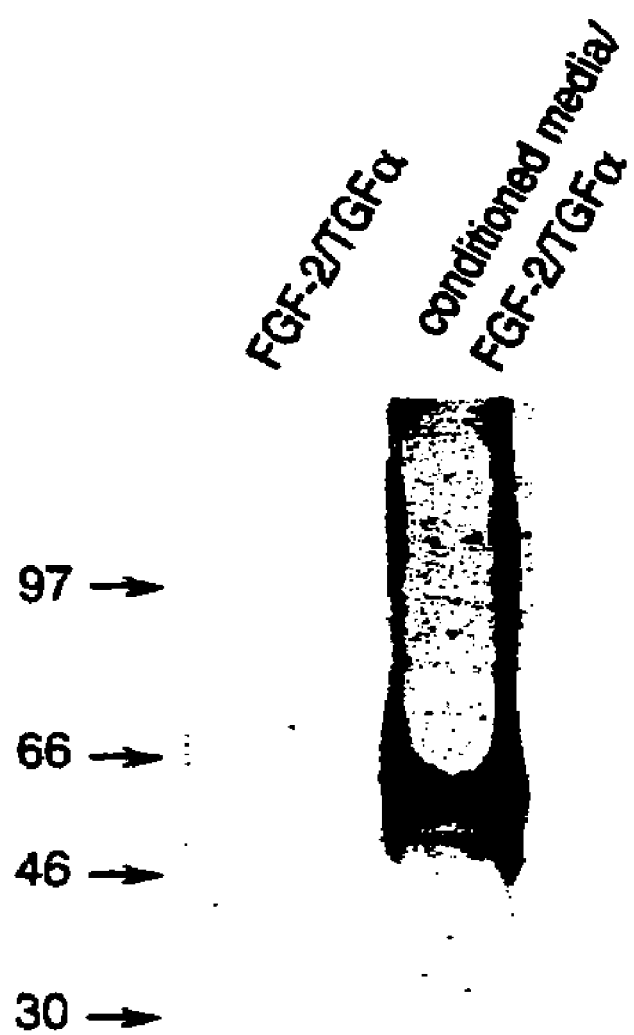
FIG. 3. Cytokeratin expression in metanephric mesenchyme. Isolated metanephric mesenchymes incubated in vitro with FGF-2/TGFα do not express cytokeratin (lane 1), but cytokeratin is detected when UB cell conditioned media is added (lane 2). Each lane of the immunoblot contains 20 μg protein.

Media Conditioned by UB Cells Triggers Epithelialization and Tubulogenesis in Isolated Metanephric Mesenchyme When isolated metanephric mesenchymes from rat renal anlage of day 13 of embryonic life ($E_{13}$) are cultured in serum free media, they undergo programmed cell death (apoptosis) in about 48 hours (Koseki et al., 1992). With the addition of FGF-2 plus TGFα (Karavanova et al., 1996) to the media, the mesenchymes grew and were able to survive more than one week in culture. However, these mesenchymes showed neither evidence of epithelial organization (FIG. 1A) nor the expression of cytokeratin (FIG. 3 lane 1), a marker of mature epithelia in the developing kidney (Lehtonen et al., 1985; Holthofer et al., 1984). In contrast, addition of media conditioned by ureteric bud cells (UB cells) plus FGF-2 and TGFα resulted in the appearance of more than 100 tubules and cysts in each mesenchyme after 7 days of incubation (FIG. 1B). These structures had characteristics of polarized epithelia including a basement membrane, basally disposed nuclei and apical junctional complexes (FIG. 2). Further, the addition of UB conditioned media stimulated the expression of cytokeratin in isolated mesenchymes (FIG. 3, lane 2). These data demonstrate that factors present in media conditioned by UB cells were able to transform metanephric mesenchyme into epithelia and induce tubulogenesis.

Figure 4:
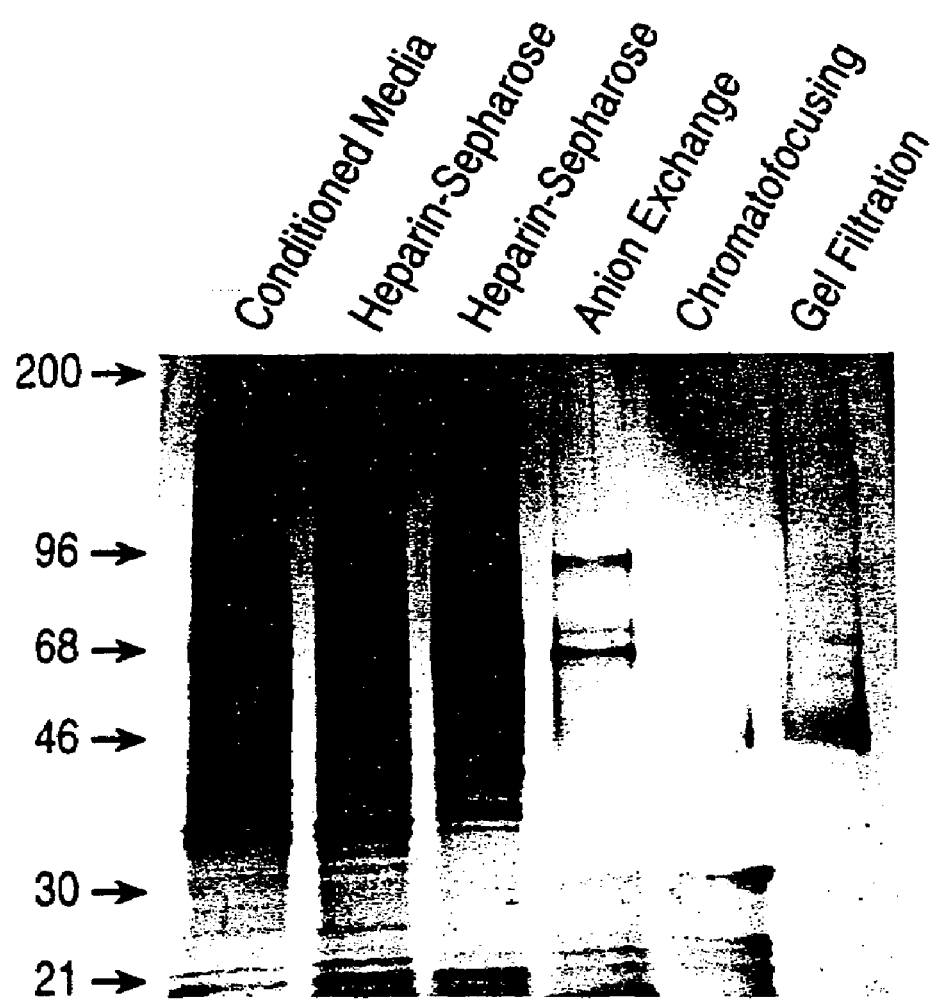
FIG. 4. Purification of LIF. Isolation of a protein from media conditioned by UB cells which stimulates mesenchymal-to-epithelial conversion and tubulogenesis. Silver stained SDS-PAGE gel shows aliquots of active fractions: UB cell conditioned media (4 μg) and active fractions after chromatography with heparin-Sepharose (4 μg), anion exchange (4 μg, equivalent of 0.4% of total protein), chromatofocusing (0.4% of total protein) and gel filtration columns (0.4% of total protein). Sequencing of the isolated 46 kDa protein identified it as LIF.
Figure 5:
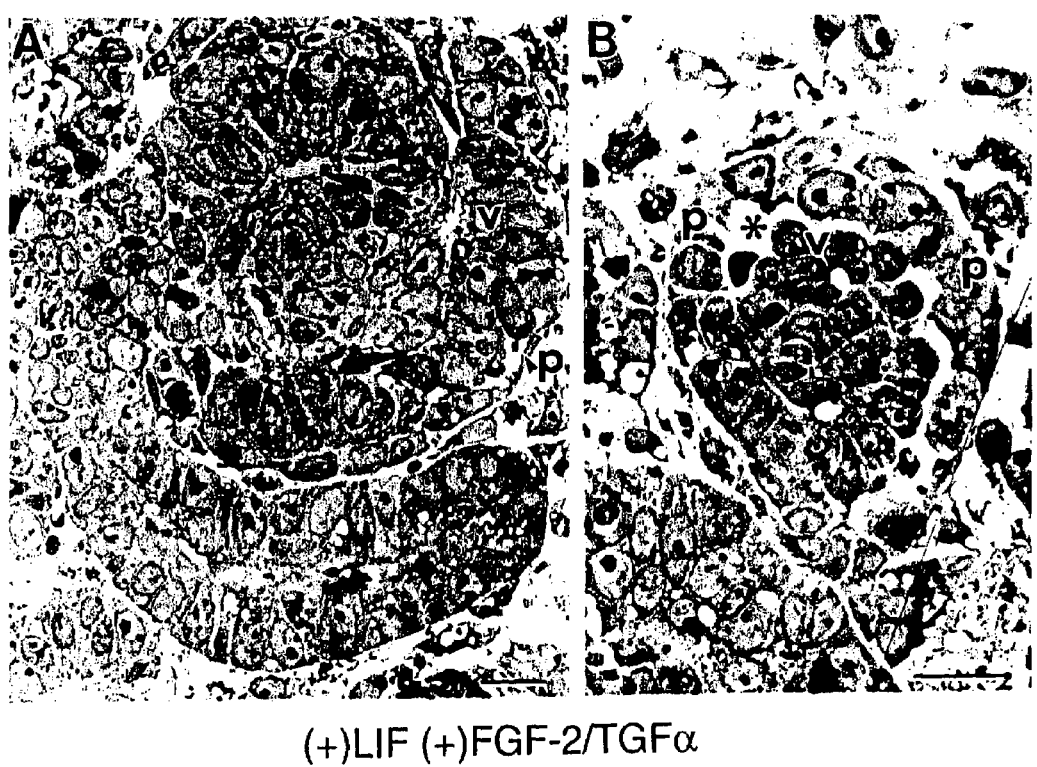
FIG. 5. Morphology of mesenchymal tubules induced by rLIF. Isolated mesenchymes were incubated with LIF (100 ng/ml) plus FGF-2/TGFα for 8 days. Noted are S-shaped tubules (A) and developing glomeruli (B), characterized by the separation of parietal ("p") from visceral ("v") epithelia by Bowman's space (*). Bars=11 μm.

Isolation of Leukemia Inhibitor Factor (LIF) from Media Conditioned by Ureteric Bud Cells As detailed in Methods, media conditioned by UB cells was initially fractionated using heparin-Sepharose chromatography (Barasch et al., 1997) and the fractions were assayed for the appearance of epithelial morphology and cytokeratins in isolated metanephric mesenchymes. While non-binding proteins were inactive, three inducing activities bound the heparin column. One activity (eluting at ~0.1 M NaCl) was selected for additional purification with a second heparin-Sepharose column followed by anion exchange, chromatofocusing, and gel filtration chromatographies (FIG. 4). Gel filtration yielded a prominent 46 kDa protein (FIG. 4) in the fraction with epithelial inducing activity. Mass spectroscopic analysis and sequencing of tryptic peptides identified the 46 kDa protein as mouse leukemia inhibitory factor (LIF).

rLIF Triggers Epithelialization, Tubulogenesis and Nephrogenesis in Isolated Metanephric Mesenchymes Confirmation that LIF causes the metanephric mesenchyme to convert into epithelia was obtained with recombinant LIF. rLIF was active at doses as little as 0.2 nM, consistent with the reported binding affinity of LIF for the LIF receptor/gp130 heterodimer (Gearing et al., 1991, 1992). In the first two days after the addition of rLIF, each mesenchyme developed 3–4 distinct cellular condensates (150–200 µM in diameter) that rapidly enlarged. Over the next three days, the cells in the condensates organized into many small clusters of cells. Longer incubations (greater than six days) resulted in the appearance of more than 100 tubules in each mesenchyme, similar to the response seen when the 46 kDa fraction isolated from UB cell conditioned media was used. A 70–100% response rate in 20 independent experiments, each with 5 individual mesenchymes, was obtained. Many of these tubules had the form of C-shaped bodies while a smaller number (approximately 10% of the tubules) were in a more developed stage of nephrogenesis (Saxen, 1987) resembling S-shaped bodies (FIG. 5A) and glomeruli (FIG. 5B). As shown in the figure, the glomeruli had visceral and parietal podocytes separated by Bowman's space (Abrahamson, 1991).

Figure 6:
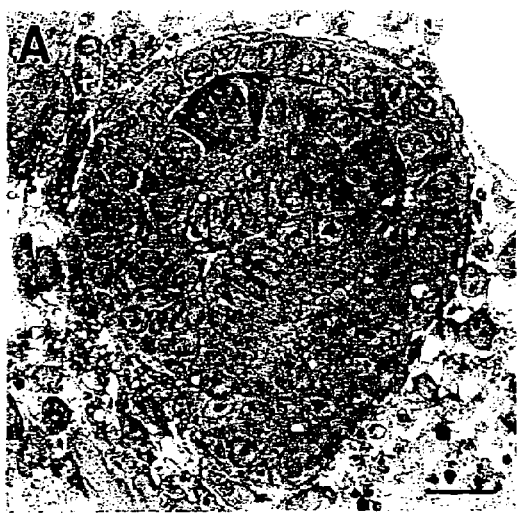
FIG. 6. rLIF induced tubules express markers of early nephrons.
A. Epithelia organize in spirals reminiscent of early nephrons in embryonic kidney. Non-epithelialized mesenchymal cells surround each body. Bar=15 μm.
B. E-cadherin is immunolocated in apical-lateral membranes of a C-shaped body. The unstained basal surface is the circumference of the body. Confocal microscopy. Bar=15 μm.
C. Segmental expression of E-cadherin. The lower pole of the C-shaped bodies is the predominant site of E-cadherin immunoreactivity, corresponding to the juxta-ureteric pole of these bodies in vivo (Cho et al., 1998). To show the outline of the entire body, the image is overexposed. Confocal microscopy. Bar=15 μm.
D. 3-D confocal projection of the E-cadherin (red-rhodamine) positive pole of a C-shaped body. Collagen IV (green-fluorescein) surrounds the base of the tubule in the extracellular matrix, while E-cadherin immunoreactivity is at apical-lateral intercellular junctions. Bar=15 m.
Figure 6:
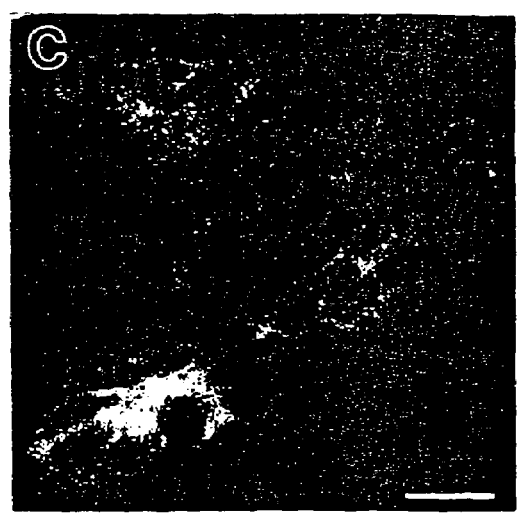
Figure 6:
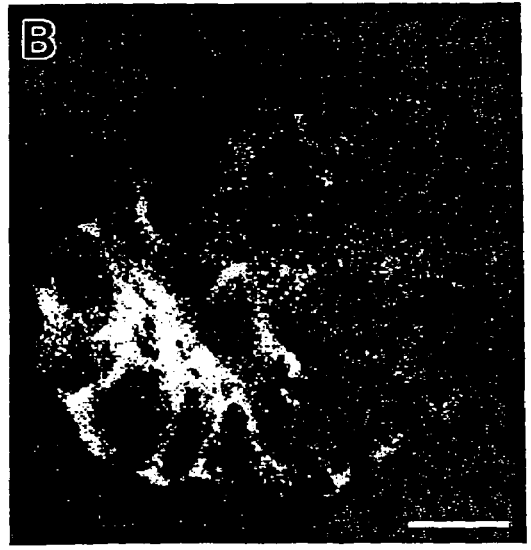
Figure 6:
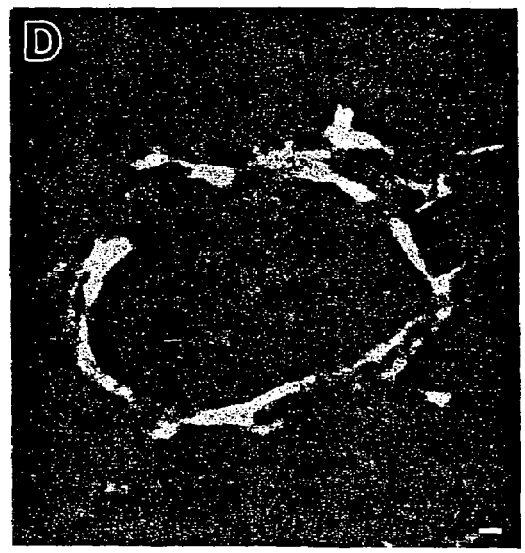
Figure 7:
FIG. 7. Aggregates, cysts and tubules induced by LIF derive from mesenchymal rather than ureteric cells as demonstrated by the localization of the mesenchymal specific transcription factor WT-1 in nuclei of the converted cells. Confocal microscopy. Bar=30 m.

To determine whether the mesenchymal structures resembling early nephrons (FIG. 5, 6A) had other characteristics of nephron precursors, we immunolocated E-cadherin (Vestweber et al., 1985; Cho et al., 1998; Klein et al., 1988) and collagen IV (Ekblom et al., 1981), two proteins with characteristic expression patterns during nephrogenesis. rLIF caused the appearance of E-cadherin along both lateral and apical cell membranes (FIG. 6B), a location that is typical of newly formed epithelia in the kidney (Vestweber et al., 1985; Klein et al., 1988). In addition, E-cadherin predominated at one pole of each epithelial aggregate (FIG. 6C), matching the protein's distribution in the developing nephron in vivo (Cho et al., 1998). Finally, each epithelial aggregate was also circumscribed by collagen IV containing matrix (FIG. 6D), the characteristic basal surface of the early nephron (Ekblom et al., 1981; Ekblom, 1981). These data, taken together, demonstrate that LIF induced nephron precursors from metanephric mesenchyme.

rLIF-induced cell aggregates, cysts and tubules expressed WT-1 (FIG. 7), demonstrating that they derived from metanephric mesenchyme (Pritchard-Jones et al., 1990; Armstrong et al., 1992) and not from fragments of ureteric bud that may have contaminated the isolated mesenchymes. The possibility that mesenchymal transformation into epithelia was due to the presence of contaminating ureteric bud cells was ruled out for the following reasons. 1) The appearance of cysts and tubules required the presence of rLIF. 2) The epithelial protein E-cadherin, which is expressed by both the ureteric bud and by mesenchymally derived epithelia, but not by non-induced metanephric mesenchyme (Vestweber et al., 1985), was undetectable both by immunoblot (FIG. 8a) and by RT-PCR (FIG. 8c) in mesenchymes incubated without rLIF, but was present when LIF was added. 3) Epithelial cytokeratins, which are expressed by both the ureteric bud and by mesenchymally derived epithelia, but not by non-induced metanephric mesenchyme (Holthofer et al., 1984), were undetectable in mesenchymes incubated without LIF, but were present when rLIF was added (FIG. 8b). 4) Isolated $E_{12}$ rat metanephric mesenchyme (not yet in contact with the ureteric bud) generated epithelia when treated with LIF (not shown). 5) Staining with a lectin specific for ureteric bud cells (dolichos bifloris; Laitinen et al., 1987) was negative in mesenchymes containing LIF-induced tubules (not shown). These data demonstrate that LIF caused mesenchymal-to-epithelia transition and tubulogenesis in metanephric mesenchymes that are free of contaminating ureteric bud cells.

Figure 8:
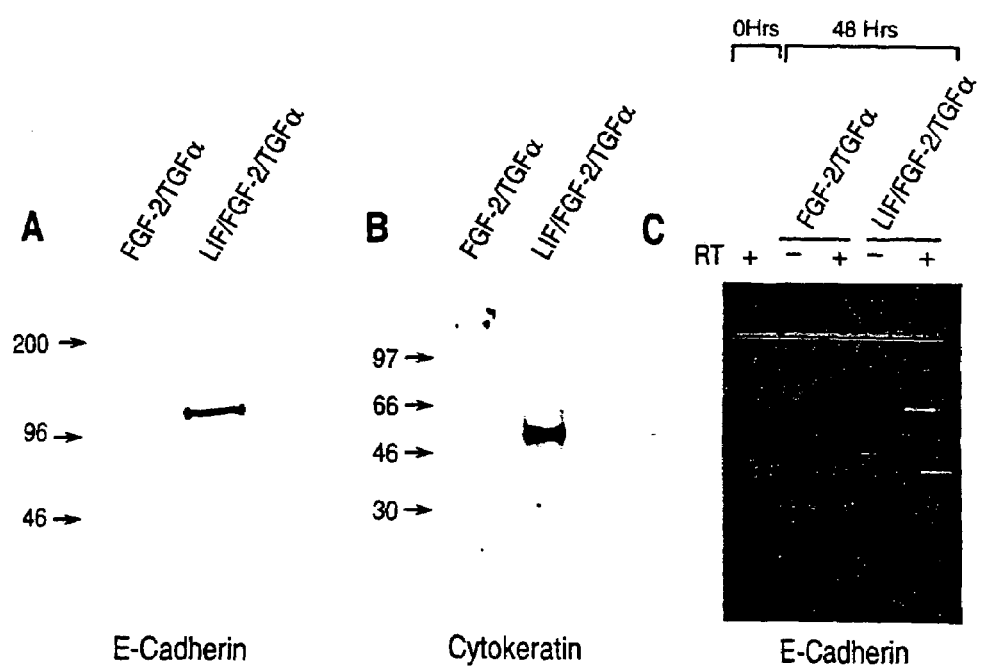
FIG. 8. Epithelia from metanephric mesenchymal cells. Metanephric mesenchymes cultured with FGF-2/TGFα do not express E-cadherin (immunoblot in A; RT-PCR in C) or cytokeratin (immunoblot in B). Addition of rLIF (100 ng/ml) induced the expression of both of these proteins. E-cadherin expression was detectable at 48 hours of treatment with LIF. Each lane of the immunoblots contains 20 μg protein. Positive and negative signs in RT-PCR respectively connote the presence and absence of reverse transcriptase in the RT-PCR reaction.

Transient Exposure of the Metanephric Mesenchyme to LIF Triggers Epithelialization Classical experiments utilized fragments of spinal cord as a substitute for the ureteric bud to trigger the conversion of isolated metanephric mesenchyme into epithelia (Nordling et al., 1971). A striking finding in those studies was that the spinal cord could be withdrawn after 24 hours of contact with mesenchyme without affecting subsequent epithelial morphogenesis. To determine whether LIF, like embryonic spinal cord, acts as a trigger for epithelialization or is tonically required to produce epithelia, we exposed mesenchymes for 24 hours to rLIF. Mesenchymes were then either washed and recultured in the presence of neutralizing antibodies to LIF or to ensure complete removal of LIF, the mesenchymes were dissociated to single cells and recultured. We found that in both conditions, incubation with rLIF for 24 hours was sufficient to initiate the conversion of the metanephric mesenchyme to epithelia. In fact, E-cadherin expression was detected by RT-PCR in metanephric mesenchymal cells within 48 hours of the addition of rLIF, demonstrating a rapid response of the mesenchyme to LIF (FIG. 8c). Thus, LIF acts like the classical heterologous inducer, spinal cord, where a short exposure with the metanephric mesenchyme is sufficient to trigger its induction. In fact, short exposure of the metanephric mesenchyme to LIF may be needed, as long term incubation of the renal anlage with LIF in vitro reduced nephron number (Bard et al., 1991).

Growth Factors are Required for LIF Induction of the Metanephric Mesenchyme

Induction of the metanephric mesenchyme in vivo by the ureteric bud includes both stimulation of growth and epithelial conversion. In our experiments, LIF stimulated mesenchymal-to-epithelial conversion had an absolute requirement for a metanephric mesenchymal growth factor; rLIF alone had no growth activity and did not induce epithelia. We tested the effect of different mesenchymal growth factors known to be synthesized by the ureteric bud and found that rLIF triggered epithelialization when combined with FGF-2, TGFα, or FGF-9 (not shown). Further, when mesenchymes were first incubated with FGF-2 plus TGFα for four days without LIF, the subsequent addition of rLIF triggered epithelialization and tubulogenesis. Since in the absence of metanephric mesenchymal growth factors, isolated metanephric mesenchymes die by apoptosis after 48 hours (Koseki et al., 1992; Barasch et al., 1997), the data suggest that competent epithelial precursors are maintained by the growth factors. In contrast, when mesenchymes were incubated with LIF for two days prior to the addition of FGF-2 plus TGFα, there was no cytokeratin expression or the appearance of epithelia, suggesting that LIF cannot maintain competent epithelial precursors. Thus, LIF must act on mesenchymal cells that were maintained, expanded or made competent to respond to LIF by a metanephric mesenchymal growth factor.

Epithelial Conversion of Metanephric Mesenchyme by gp130 Ligands

LIF is one member of the interleukin-6 (IL-6) family that signals through the LIF receptor/gp130 heterodimer (Taga et al., 1989; Ip et al., 1992). To determine whether activation of the heterodimer by family members other than LIF could also induce epithelia, we treated isolated metanephric mesenchymes with oncostatin M, cardiotrophin, or ciliary neuronotrophic factor. Each one of these molecules was able to stimulate metanephric mesenchyme to convert to epithelia and generate tubules (50–100 ng/ml gave a 70–100% response rate in 4 independent experiments). To determine whether activation of gp130 receptor without activation of the LIF receptor was sufficient to convert mesenchyme to epithelia, we cultured metanephric mesenchymes with IL-6. While IL-6 alone (50 ng/ml) had no effect, when added together with a soluble form of its receptor (5 µg/ml; Taga et al., 1989), IL-6 produced mesenchymal-to-epithelial conversion and tubulogenesis. These data demonstrate that epithelialization of the metanephric mesenchyme may be triggered by ligands that activate either the LIF receptor/gp130 complex or gp130 independently of LIF receptors.

Location of LIF and Receptor in Embryonic Kidney

Figure 9:
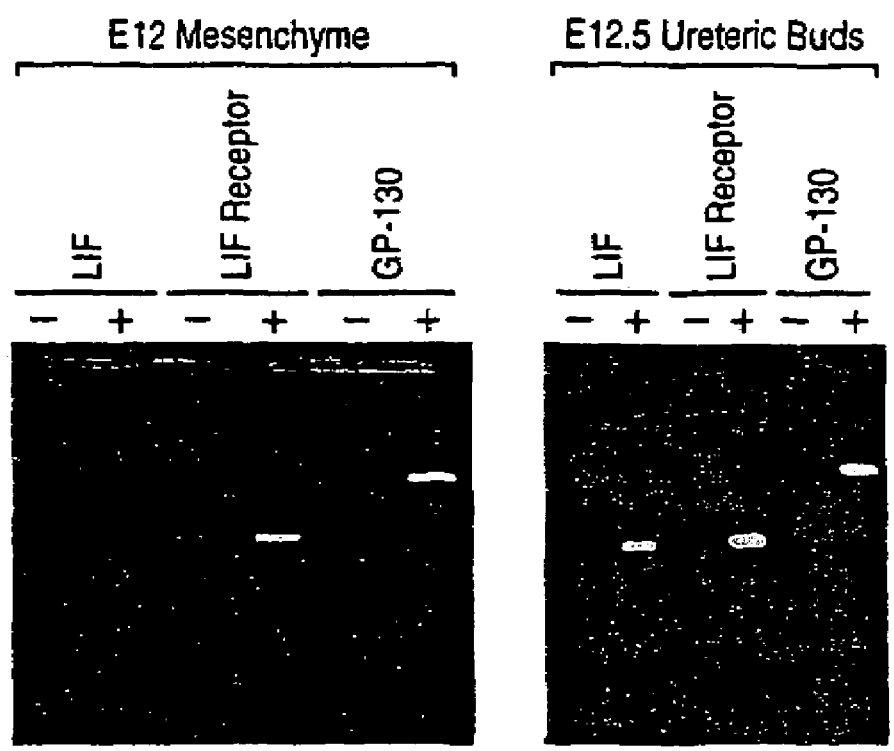
FIG. 9. The ureteric bud expresses LIF upon leaving the Wolffian duct and invading the metanephric mesenchyme at day 12.5 of embryonic life ($E_{12.5}$). In contrast, metanephric mesenchyme ($E_{12}$) does not express LIF. Both compartments express gp-130 and LIF receptors. Positive and negative signs in RT-PCR respectively connote the presence and absence of reverse transcriptase in the RT-PCR reaction.

The essential role of the ureteric bud in the conversion of metanephric mesenchyme to epithelia in vivo (Grobstein, 1955) suggests that the bud is the initial source of inducing molecules. To examine whether the in vivo expression pattern of LIF and its receptors is compatible with LIF being such a molecule, we performed RT-PCR of metanephric mesenchyme just prior to the invasion of the ureteric bud ($E_{12}$) and of ureteric buds just after their extension from the Wolffian duct ($E_{12.5}$). While LIF receptor and gp-130 were readily detectable in metanephric mesenchyme, LIF was not expressed (FIG. 9). In contrast, ureteric bud isolated at $E_{12.5}$ expressed both LIF and its receptors. These data demonstrate that the ureteric bud is the initial source of LIF for the mesenchyme.

Involvement of STAT-3

LIF, cardiotrophin and the other members of the IL-6 family activate the second messenger STAT-3 in the developing kidney. We have purified to homogeneity from ureteric bud cells two additional factors that cause metanephric mesenchyme to convert to epithelia. These factors, like the IL-6 cytokines, also activate STAT-3. In addition, we found that interleukin-17, which also converts mesenchyme to epthelia, is a STAT-3 activator. These data show that the induction of the kidney tubules by many hormones present in the kidney (both IL-6 family members and non-family members) activate the same pathway that we initially identified with the IL-6 family of cytokines.

In vivo Testing of IL-6 Cytokines

We found that the receptors for the IL-6 family of cytokines are expressed in the adult kidney, particularly in the proximal tubule. This part of the nephron is typically damaged in many forms of acute tubular necrosis. This finding led to the development of animal models of acute tubular necrosis and evaluation of the use of IL-6 cytokines to rescue damaged tubules.

Interpretation Of The Results

Since impeding formation of the ureteric bud prevented nephrogenesis in chicken embryos, Boyden (1927) and Gruenwald (1943) suggested that the ureteric bud is critical for avian metanephric mesenchymal development. Similarly, surgical extirpation of the ureteric bud prevented development of the mouse metanephric mesenchyme (Grobstein, 1955). Moreover, since mesenchymal-to-epithelial conversion and nephrogenesis could be triggered by tissues other than the ureteric bud (e.g., spinal cord), Gruenwald (1943) and Grobstein (1955) concluded that molecules exogenous to the mesenchyme are needed to initiate its development (i.e., induction) and that the ureteric bud is their source in vivo. However, despite much work over the last 70 years (Schuchardt et al., 1994), the specific identities of the ureteric bud molecules capable of inducing the metanephric mesenchyme have not been established prior to the present application.

Recently, Herzlinger et al. (1994) demonstrated that isolated metanephric mesenchyme converted into epithelia when incubated with Wnt-1 expressing cell lines and suggested that Wnts may be mesenchymal inducers released from the ureteric bud in vivo. However, the specific inducing activities of different Wnts, as well as their localization in the embryonic kidney, suggest that Wnts may not be ureteric factors responsible for metanephric induction. For example, while Wnt-11 is expressed by tips of the ureteric bud adjacent to mesenchyme undergoing epithelial conversion (Kispert et al., 1996), fibroblasts expressing Wnt-11 do not trigger epithelialization of isolated metanephric mesenchyme (Kispert et al., 1998). In contrast, although Wnt-1 and Wnt-4 expressing fibroblasts can induce isolated metanephric mesenchyme (Kispert et al., 1998), Wnt-1 is not expressed in the kidney and Wnt-4 is not expressed by the ureteric bud; instead, mesenchymal cells surrounding the tips of the ureteric bud express Wnt-4 (Stark et al., 1994). Because deletion of Wnt-4 blocks induction of the metanephric mesenchyme in vivo (Stark et al., 1994), Kispert et al. (1998) suggested that Wnt signaling is most critical within the mesenchyme rather than between it and the ureteric bud.

It should be noted that the above mentioned Wnt proteins are insoluble and thus not available for therapeutic use. The present disclosure documents the first pure factor that can produce kidney nephrons and is available for therapeutic use in pure form.

To study the functions of the ureteric bud and to identify factors that may induce the metanephric mesenchyme, we developed ureteric bud cell lines (Barasch et al., 1996). We now find that UB cells secrete factors that trigger induction of isolated metanephric mesenchymes. Isolation and sequencing of one of these activities identified it as LIF. rLIF had identical activity as our purified fraction, causing the metanephric mesenchyme to convert to epithelia, produce tubules and develop early nephrons. At the time the ureteric bud invades the metanephric mesenchyme, LIF is expressed by the bud and LIF receptors are expressed by the mesenchyme. Thus, LIF may represent a class of ureteric inducers that trigger mesenchymal induction during kidney development.

The activity of LIF in kidney mesenchyme is consistent with the activity of cytokines of the IL-6 family in many cell types. For example, Ml leukemic cells rapidly differentiate when exposed to LIF (Metcalf et al., 1988) and LIF and ciliary neuronotrophic factor can rapidly induce the generation of astrocytes (Bonni et al., 1997), oligo-dendrocytes (Mayer et al., 1994) or sensory neurons (Murphy et al., 1991) from different precursor cells which otherwise remain undifferentiated or produce other derivatives (Murphy et al., 1993, 1994). Also consistent with our findings are experiments that demonstrate that the target of LIF receptor activation, STAT-3, may be essential for epithelial and endothelial morphogenesis. Isolated epithelia produce tubules upon STAT-3 activation and blockade of STAT-3 signaling inhibits tubulogenesis (Boccaccio et al., 1998). Similarly, formation of endothelial capillaries is stimulated by leptin activation of STAT-3 (Sierra-Honigmann et al., 1998). Our data indicate that the induction of the kidney tubules by many hormones present in the kidney (both IL-6 family members and non-family members) occurs via the STAT-3 pathway.

We previously found that FGF-2 stimulates growth of the metanephric mesenchyme and can maintain epithelial precursors for many days in culture (Barasch et al., 1997). In contrast, LIF has no growth activity. However, the combination of LIF and a metanephric mesenchymal growth factor was absolutely required to induce epithelia from mesenchyme. A number of mechanisms may explain this dual requirement. The simplest explanation is that FGF-2 and TGFá act as survival factors for epithelial precursors in which LIF activates an epithelial program of gene expression. A second possibility is that the mesenchymal growth factors may trigger a variety of changes in epithelial precursors (e.g. upregulating LIF receptors) that permit LIF induction. Finally, the mesenchymal growth factors may trigger the expression of a mesenchymal factor (such as Wnt-4), which in combination with LIF triggers mesenchymal induction.

The role of LIF and other members of the IL-6 family in renal development must now be examined in animals in which these cytokines are deleted. There are a number of problems in this analysis, however. While the single deletion of LIF or other family members produces only subtle abnormalities, the combined deletion of two of these cytokines enhances the abnormal phenotype (Sendtner et al., 1996). The ureteric bud expresses LIF (FIG. 9) and several other cytokines of the IL-6 family (Sheng et al., 1996) and each of these cytokines can induce the metanephric mesenchyme. Hence, developmental abnormalities from deletion of a single cytokine may be subtle and difficult to detect.

In contrast to the subtle phenotypes of single deletions of IL-6 family members, deletion of their receptors results in embryonic or perinatal lethality. Both LIF receptor—(Li et al., 1995; Ware et al., 1995) and gp130— (Yoshida et al., 1996) deleted animals have defects in many organs, but their renal phenotype has not been investigated. Defective kidney development is predicted to be less likely to occur in LIF receptor deletions rather than in gp130 deleted animals, because signaling by IL-6 cytokines that are independent of the LIF receptor (e.g., oncostatin) would also be abrogated.

Our findings have led to the development of animal models of acute tubular necrosis and evaluation of the use of IL-6 cytokines to rescue damaged tubules.

The present application discloses that the combination of LIF with mesenchymal growth factors induces the conversion of mesenchyme to epithelia and the development of early nephrons. These data suggest that stimulation of mesenchymal growth and its conversion to epithelia results from the coordinate actions of different sets of ureteric bud factors.

REFERENCES

Abrahamson, D. 1991. Glomerulogenesis in the developing kidney. *Sem. In Nephrology.* 11:375–389.

Altschul, S. F., W. Gish, W. Miller, E. W. Meyers, and D. J. Lipman. 1990. Basic local alignment search tool. *J. Mol. Biol.* 215: 403–410.

Armstrong, J. F., K. Pritchard-Jones, W. A. Bickmore, N. D. Hastie, and J. B. L. Bard. 1992. The expression of the Wilms? tumour gene, WT-1, in the developing mammalian embryo. *Mech. Of Devel.* 40: 85–97.

Barasch, J., L. Pressler, J. Connor, and A. Malik. 1996. A ureteric bud cell line induces nephrogenesis in two steps by two distinct signals. *Am. J. Physiol.* 271: F50–F61.

Barasch, J., J. Qiao, G. McWilliams, D. Chen, J. A. Oliver, and D. Herzlinger. 1997. Ureteric bud cells secrete multiple factors, including bFGF, which rescue renal progenitors from apoptosis. *Am. J. Physiol.* 273: F757–F767.

Barasch, J., J. Yang, H. Erdjument-Bromage, P. Tempst, Leung, J. Oliver. 1999. Tissue inhibitor of metalloproteinase-2 stimulates mesenchymal growth and regulates epithelial branching during morphogenesis of the rat metanephros. *J. Clin. Invest.*, in press.

Bard, J. B. L. and A. Ross. 1991. LIF, the ES-cell inhibition factor, reversibly blocks nephrogenesis in cultured mouse kidney rudiments. *Development* 113: 193–198.

Boccaccio, C., M. Ando, L. Tamagnone, A. Bardelli, P. Michielli, C. Battistini, and P. Comoglio. 1998. Induction of epithelial tubules by growth factor HGF depends on the STAT pathway. *Nature* 391: 285–288.

Bonni, A., Y. Sun, M. Nadal-Vicens, A. Bhatt, D. A. Frank, I. Rozovsky, N. Stahl, G. Yancopoulos, and M. E. Greenberg. 1997. Regulation of gliogenesis in the central nervous system by the JAK-STAT signaling pathway. *Science* 278: 477–483.

Boyden, E. A. 1927. Experimental obstruction of the mesonephric duct. *Proc. Soc. Exp. Biol. Med.* 24:572–576.

Cho E. A., L. T. Patterson, W. T. Brookhiser, S. Mah, C. Kintner, and G. Dressler. 1998. Differential expression and function of cadherin-6 during renal epithelium development. *Development* 125: 803–812.

Ekblom, P., E. Lehtonen, L. Saxen, and R. Timpl. 1981. Shift in collagen type as an early response to induction of the metanephric mesenchyme. *J. Cell Biol.* 89: 276–283.

Ekblom, P. 1981. Formation of basement membrane in the embryonic kidney. *J. Cell Biol.* 91: 1–10.

Ekblom, P. 1989. Developmentally regulated conversion of mesenchyme to epithelium. *FASEB J.* 3: 2141–50.

Elicone, C., M. Lui, S. Geromanos, H. Erdjument-Bromage, and P. Tempst. 1994. Microbore reversed-phase high performance liquid chromatographic purification of peptides for combined chemical sequencing-laser desorption mass spectrometric analysis. *J. Chromatogr.* 676: 121–137.

Erdjument-Bromage, H., M. Lui, L. Lacomis, A. Grewal, R. S. Annan, D. McNulty, S. A. Carr, and P. Tempst. 1998. Examination of micro-tip reversed-phase liquid chromatographic extraction of peptide pools for mass spectrometric analysis. *J. Chromatogr.* 826: 167–181.

Faulds, G., D. Fishman, P. Woo, and S. Humphries. 1998. Novel FokI polymorphism in the 5' flanking region of the human IL-6 gene. GENBANK, Accesion No. AF048692.1.

Gearing, D. P., C. J. Thut, T. VandeBos, S. D. Gimpel, P. B. Delaney, J. King, V. Price, D. Cosman, and M. P. Beckmann. 1991. Leukemia inhibitory factor receptor is structurally related to the IL-6 signal transducer, gp130. *EMBO J.* 10: 2839–2848.

Gearing, D. P., M. R. Comeau, D. J. Friend, S. D. Gimpel, C. J. Thut, J. McGourty, K. K. Brasher, A. King, S. Gillis, B. Mosley, S. F. Ziegler, and D. Cosman. 1992. The IL-6 signal transducer, gp130: an Oncostatin M receptor and affinity converter for the LIF receptor. *Science* 255: 1434–1437.

Gilbert, T., C. Cibert, J. Vilar, E. Moreau, G. Geraud, C. Merlet-Benichou. 1996. Early defect in branching morphogenesis of the ureteric bud in induced nephron deficit. *Kid. Int.* 50:783–795.

Grobstein, C. 1955. Inductive interaction in the development of the mouse metanephros. *J. Exp. Zool.* 130:319–339.

Gruenwald, P. 1943. Stimulation of nephrogenic tissue by normal and abnormal inductors. *Anat. Rec.* 86:321–334.

Herzlinger, D., C. Koseki, T. Mikawa, and Q. Al-Awqati. 1992. Metanephric mesenchyme contains multipotent stem cells whose fate is restricted after induction. *Development* 114: 565–572.

Herzlinger, D., J. Qiao, D. Cohen, N. Ramakrishna, and A. M. C. Brown. 1994. Induction of kidney epithelial morphogenesis by cells expressing Wnt-1. *Develop. Biol.* 166:815–818.

Hibi, M., M. Murakami, M. Saito, T. Hirano, T. Taga, and T. Kishimoto. 1990. Molecular cloning and expression of an IL-6 signal transducer, gp130. *Cell* 63:1149–1157.

Holthofer, H., A. Miettinen, V. P. Lehto, E. Lehtonen, and I. Virtanen. 1984. Expression of vimentin and cytokeratin types of intermediate filament proteins in developing and adult human kidneys. *Lab. Invest.* 50: 552–559.

Ip, N.Y., S. H. Nye, T. G. Boulton, S. Davis, T. Taga, Y. Li, S. J. Birren, K. Yasukawa, T. Kishimoto, D. J. Anderson, N. Stahl and G. D. Yancopoulos. 1992. CNTF and LIF act on neuronal cells via shared signaling pathways that involve the IL-6 signal transducing receptor component gp130. *Cell* 69: 1121–1132.

Karavanova, I., L. Dove, J. Resau, and A. Perantoni. 1996. Conditioned media from a rat ureteric bud cell line in combination with bFGF induces complete differentiation of isolated metanephric mesenchyme. *Development* 122: 4159–4167.

Kispert, A., S. Vainio, L. Shen, D. H. Rowitch, and A. P. McMahon. 1996. Proteoglycans are required for maintenance of Wnt-11 expression in the ureteric tips. *Development* 122: 3627–3637

Kispert, A., S. Vainio, A. P. McMahon. 1998. Wnt-4 is a mesenchymal signal for epithelial transformation of metanephric mesenchyme in the developing kidney. *Development* 125: 4225–4234.

Klein, G., M. Langegger, C. Goridis, and P. Ekblom. 1988. Neural cell adhesion molecules during embryonic induction and development of the kidney. *Development* 102: 749–761.

Koseki, C., D. Herzlinger, and Q. Al-Awqati. 1992. Apotosis in metanephric development *J. Cell Biol.* 119: 1327–33.

Kurokawa, T., R. Sasada, M. Iwane, and K. Igarashi. 1987. Cloning and expression of cDNA encoding human basic fibroblast growth factor. *FEBS Lett.* 213: 189–194.

Laitinen, L., I. Virtanen, and L. Saxen. 1987. Changes in the glycosylation pattern during embryonic development of mouse kidney as revealed with lectin conjugates. *J. Histochem. and Cytochem.* 35: 55–65.

Lehtonen, E., I. Virtanen, and L. Saxen. 1985. Reorganization of intermediate cytoskeleton in induced metanephric mesenchyme cells is independent of tubule morphogenesis. *Devel. Biol.* 108: 481–490.

Li, M., M. Sendtner, A. Smith. 1995. Essential function of LIF receptor in motor neurons. *Nature* 378:724–727.

Lui M., P. Tempst, and H. Erdjument-Bromage. 1996. Methodical analysis of protein-nitrocellulose interactions to design a refined digestion protocol. *Anal. Biochem.* 241: 156–166.

Malik, N., J. C. Kallestad, N. L. Gunderson, S. D. Austin, M. G. Neubauer, V. Ochs, H. Marquardt, J. M. Zarling, M. Shoyab, C.-M. Wei, P. S. Linsley, and T. M. Rose. 1989. Molecular cloning, sequence analysis, and functional expression of a novel growth regulator, oncostatin M. *Mol. Cell. Biol.* 9: 2847–2853.

Mayer, M., Bhakoo, K., and M. Noble. 1994. Ciliary neurotrophiic factor and leukemia inhibitory factor promote the generation, maturation and survival of oligodendrocytes in vitro. *Development* 120:143–153.

Metcalf, D., D. J. Hilton, and N. A. Nicola. 1988. Clonal analysis of the actions of the murine leukemia inhibitory factor on leukemic and normal murine hemopoietic cells. *Leukemia* 2: 216–221.

Miyamoto, M., K. Naruo, C. Seko, S. Matsumoto, T. Kondo, and T. Kurokawa. 1993. Molecular cloning of a novel cytokine cDNA encoding the ninth member of the fibroblast growth factor family, which has a unique secretion property. *Mol. Cell Biol.* 13: 4251–4259.

Moreau, J. F., D. D. Donaldson, F. Bennett, J. Witek-Giannotti, S. C. Clark, and G. G. Wong. 1988. Leukaemia inhibitory factor is identical to the myeloid growth factor human interleukin for DA cells. *Nature* 336:690–692.

Murphy, M., K. Reid, D. J. Hilton, and P. F. Bartlett. 1991. Generation of sensory neurons is stimulated by leukemia inhibitory factor. *Proc. Natl. Acad. Sci. USA* 88:3498–3501.

Murphy, M., K. Reid, M. A. Brown, P. F. Bartlett. 1993. Involvement of leukemia inhibitory factor and nerve growth factor in the development of dorsal root ganglion neurons. *Development* 117:1173–1182.

Murphy, M., K. Reid, M. Ford, J. B. Furness, and P. F. Bartlett. 1994. FGF-2 regulates proliferation of neural crest cells, with subsequent neuronal differentiation regulated by LIF or related factors. *Development* 120: 359–3528.

Nordling, S., H. Miettinen, J. Wartiovaara, and L. Saxen. 1971. Transmission and spread of embryonic induction: temporal relationship in transfilter induction of kidney tubules in vitro. *J. Embrol. Exp. Morphol.* 26: 231–252.

Perantoni, A., L. Dove and I. Karavanova. 1995. Basic fibroblast growth factor can mediate the early inductive events in renal development. *Proc. Natl. Acad. Sci. USA.* 92: 4696–4700.

Pritchard-Jones, K., S. Fleming, D. Davidson, W. Bickmore, D. Porteous, C. Gosden, J. Bard, A. Buckler, J. Pelletier, D. Housman, V. van Heyningen, and N. Hastie. 1990. The candidate Wilms? tumour gene is involved in genitourinary development. *Nature* 346: 194–196.

Sakuri, H., E. J. Barros, T. Tsukamoto, J. Barasch, S. K. Nigam. 1997. An in vitro tubulogenesis system using cell lines derived from the embryonic kidney shows dependence on multiple soluble growth factors. *Proc. Natl. Acad. Sci.* 94:627–6284.

Sariola, H., P. Ekblom, S. Henke-Fahle. 1989. Embryonic neurons as in vitro inducers of differentiation of nephrogenic mesenchyme. *Devel. Biol.* 132:271–281.

Saxen, L. 1987. Organogenesis of the Kidney. University Press, Cambridge.

Schuchardt, A., V. D'Agati, L. Larsson-Blomberg, F. Costantini, and V. Pachnis. 1994. Defects in the kidney and the enteric nervous system of mice lacking the tyrosine kinase receptor ret. *Nature* 367: 380–383.

Sendtner, M., R. Gotz, B Holtmann, J. L. Escary, Y. Masu, P. Carroll, E. Wolf, G. Brem, P. Brulet, H. Thoenen. 1996. Cryptic physiological trophic support of motoneurons by LIF revealed by double gene targeting of CNTF and LIF. *Current Biol.* 6:686–694.

Sheng, Z., D. Pennica, W. I. Wood, K. R. Chien. 1996. Cardiotrophin-1 displays early expression in the murine heart tube and promotes cardiac myocyte survival. *Development* 122: 419–428.

Sierra-Honigmann, M. R., A. K. Nath, C. Murakami, G. Garcia-Cardena, A. Papapetropoulos, W. C. Sessa, L. A. Madge, J., S. Schechner, M. B. Schwabb, P. J. polyerini, J. R. Flores-Riveros. 1998. Biological action of leptin as an angiogenic factor. *Science* 281: 1683–1686.

Stark, K., S. Vainio, G. Vassileva, A. P. McMahon. 1994. Epithelial transformation of metanephric mesenchyme in the developing kidney regulated by Wnt-4. *Nature* 372: 679–683.

Stetler-Stevenson, W. G., P. D. Brown, M. Onisto, A. T. Levy, and L. A. Liotta. 1990. Tissue inhibitor of metalloproteinases-2 (TIMP-2) mRNA expression in tumor cell lines and human tumor tissues. *J. Biol. Chem.* 265: 13933–13938.

Taga, T., M. Higi, Y. Hirata, K. Yamasaki, K. Yasukawa, T. Matsuda, T. Hirano, and T. Kishimoto. 1989. Interleukin-6 triggers the association of its receptor with a possible signal transducer, gp130. *Cell* 58: 573–581.

Tempst, P., S. Geromanos, C. Elicone, and H. Erdjument-Bromage. 1994. Improvements in microsequencer performance for low picomole sequence analysis. *METHODS Companion Meth. Enzym.* 6: 248–261.

Vestweber, D., R. Kemler, and P. Ekblom. 1985. Cell adhesion molecule uvomorulin during kidney development. *Devel. Biol.* 112: 213–21.

Ware, C., M. C. Horowitz, B. R. Renshaw, J. S. Hunt, D. Liggitt, S. A. Koblar, B. C. Gliniak, H. J. McKenna, T. Papayannopoulou, B. Thoma, L. Cheng, P. J. Donovan, J. J. Peschon, P. F. Bartlett, C. R. Willis, B. D. Wright, M. K. Carpenter, B. L. Davison, and D. P. Gearing. 1995. Targetted disruption of the low affinity leukemia inhibitory factor gene causes placental, skeletal, neural and metabolic defects and results in perinatal death. *Development* 121:1283–1299.

Wong, G. G., J. Witek-Giannotti, R. M. Hewick, S. C. Clark, and M. Ogawa. 1988. Interleukin 6: identification as a hematopoietic colony-stimulating factor. *Behring Inst. Mitt.* 83: 40–47.

Yoshida, K., T. Taga, M. Saito, S. Suematsu, A. Kumanogoh, T. Tanaka, H. Fujiwara, M. Hirata, T. Yamagami, T. Nakahata, T. Hirabayashi, Y. Yoneda, K. Tanaka, W-Z. Wang, C. Mori, K. Shiota, N. Yoshida, and T. Kishimoto. 1996. Targeted disruption of gp130, a common signal transducer for the interleukin-6 family of cytokines, leads to myocardial and hematological disorders. *Proc. Natl. Acad. Sci. USA.* 93:407–411.

What is claimed is:

1. A method of preserving a kidney for transplantation which comprises contacting the kidney, in the presence of a growth factor, with an amount of a gp130 receptor ligand effective to preserve the kidney wherein the gp130 receptor ligand is chosen from the group consisting of a leukemia inhibitory factor, a cardiotrophin, a ciliary neuronotrophic factor, an interleukin-6, a polypeptide comprising consecutive amino acids having a sequence identical to the sequence of a naturally occurring human leukemia inhibitory factor, and a polypeptide comprising consecutive amino acids having a sequence identical to the sequence of a naturally occurring human growth factor selected from the group consisting of a TGFα, a FGF-2, a FGF-9, a TIMP-1, TIMP-2 and mixtures thereof.

2. The method of claim 1, wherein the gp130 receptor ligand is a leukemia inhibitory factor.

3. The method of claim 1, wherein the effective amount of the gp130 receptor ligand is an amount from about 5 ng/ml to about 200 ng/ml.

4. The method of claim 1, wherein the growth factor is selected from the group consisting of TGFα, a FGF-2, or FGF-9 and the effective amount of TGFα, a FGF-2, or FGF-9 is an amount from about 1 ng/ml to about 100 ng/ml.

5. The method of claim 1, wherein the growth factor is TIMP-1 or TIMP-2 and the effective amount of TIMP-1 or TIMP-2 is an amount from about 200 ng/ml to about 2 μg/ml.

* * * * *